(12) United States Patent
Daphna et al.

(10) Patent No.: US 11,890,183 B2
(45) Date of Patent: Feb. 6, 2024

(54) CORNEAL IMPLANT WITH PERIPHERAL SKIRT

(71) Applicant: EyeYon Medical Ltd., Nes Ziona (IL)

(72) Inventors: Ofer Daphna, Beit Elazari (IL); Nahum Ferera, Petah Tikva (IL)

(73) Assignee: EyeYon Medical Ltd., Nes Ziona (IL)

( * ) Notice: Subject to any disclaimer, the term of this patent is extended or adjusted under 35 U.S.C. 154(b) by 219 days.

(21) Appl. No.: 17/299,037

(22) PCT Filed: Nov. 25, 2019

(86) PCT No.: PCT/IB2019/060122
§ 371 (c)(1),
(2) Date: Jun. 2, 2021

(87) PCT Pub. No.: WO2020/115605
PCT Pub. Date: Jun. 11, 2020

(65) Prior Publication Data
US 2022/0023030 A1    Jan. 27, 2022

Related U.S. Application Data

(63) Continuation of application No. 16/207,142, filed on Dec. 2, 2018, now abandoned.

(51) Int. Cl.
*A61F 2/14*     (2006.01)
*A61F 2/00*     (2006.01)

(52) U.S. Cl.
CPC .... *A61F 2/1453* (2015.04); *A61F 2002/0081* (2013.01); *A61F 2250/0024* (2013.01)

(58) Field of Classification Search
CPC ............ A61F 2/1453; A61F 2002/0081; A61F 2250/0024; A61F 2/145; A61F 2/1451; A61F 2/142
See application file for complete search history.

(56) References Cited

U.S. PATENT DOCUMENTS

| | | | | |
|---|---|---|---|---|
| 4,612,012 A | * | 9/1986 | White | A61F 2/142 623/5.14 |
| 4,865,601 A | | 9/1989 | Caldwell | |
| 5,300,116 A | * | 4/1994 | Chirila | A61F 2/142 623/5.14 |
| 2006/0287721 A1 | * | 12/2006 | Myung | A61F 2/15 264/1.7 |

(Continued)

FOREIGN PATENT DOCUMENTS

| | | |
|---|---|---|
| EP | 2067453 | 6/2009 |
| SU | 1160623 | 10/1987 |

(Continued)

OTHER PUBLICATIONS

PCT Search Report and Written Opinion PCT/IB2019/060122, dated Mar. 11, 2020.
Office action, U.S. Appl. No. 16/207,142, dated Apr. 27, 2020.

*Primary Examiner* — Javier G Blanco
(74) *Attorney, Agent, or Firm* — Dekel Patent Ltd.; David Klein

(57) ABSTRACT

A corneal implant (10) includes a central portion (12) and a peripheral skirt (14) extending outwards from the central portion (12), and at least a portion of the peripheral skirt (14) includes a mesh (16).

7 Claims, 1 Drawing Sheet

(56) References Cited

U.S. PATENT DOCUMENTS

| | | | |
|---|---|---|---|
| 2006/0290883 A1* | 12/2006 | Rosenthal | G02C 7/047 351/159.12 |
| 2007/0168025 A1* | 7/2007 | Darougar | A61F 2/142 623/5.14 |
| 2007/0179605 A1 | 8/2007 | Myung | |
| 2012/0173325 A1* | 7/2012 | Johri | G06Q 20/401 705/17 |
| 2017/0319330 A1 | 11/2017 | Guerreschi | |

FOREIGN PATENT DOCUMENTS

| | | | | |
|---|---|---|---|---|
| WO | 2004/105588 | 12/2004 | | |
| WO | WO-2006009490 A1 * | 1/2006 | | A61F 2/142 |

* cited by examiner

CORNEAL IMPLANT WITH PERIPHERAL SKIRT

FIELD OF THE INVENTION

The present invention relates generally to corneal implants, such as for treating an over-hydrated, edematous cornea, and particularly to a corneal implant with a peripheral skirt that improves adhesion of the implant to the corneal tissue.

BACKGROUND OF THE INVENTION

U.S. Pat. Nos. 8,109,997 and 8,500,803 to Daphna describe bonding a hydrophobic pseudo-endothelial implant to a posterior portion of the cornea adjacent the aqueous humor with a binding agent. The implant serves as a water barrier enabling dehydration of the cornea, and may be used in the treatment of an edematous cornea.

The adhesion of an implant to corneal tissue without sutures or mechanical fasteners poses a challenge. The adhesive materials must be compatible with the ocular environment and yet must provide good adhesion for a long time without degradation in the ocular quality of the eye.

SUMMARY OF THE INVENTION

The present invention relates to a corneal implant with a peripheral skirt that improves adhesion of the implant to the corneal tissue, as is described more in detail hereinbelow.

In one aspect of the invention, the corneal implant has a central portion of about 4 mm in diameter ("about" is ±10%) and the peripheral skirt is outwards of the central portion. The central portion is transparent and may or may not have optical properties, such as positive or negative magnification, astigmatism correction, refraction adjustment and others. The peripheral skirt may be transparent but can instead be opaque. In one aspect of the invention, the peripheral skirt includes a mesh that enables cell growth in and through the mesh to enhance adhesion of the implant to the cornea. The peripheral skirt may be thinner or thicker than the central portion.

There is provided in accordance with an embodiment of the present invention a corneal implant including a central portion and a peripheral skirt extending outwards from the central portion, wherein at least a portion of the peripheral skirt includes a mesh.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Figure 1:
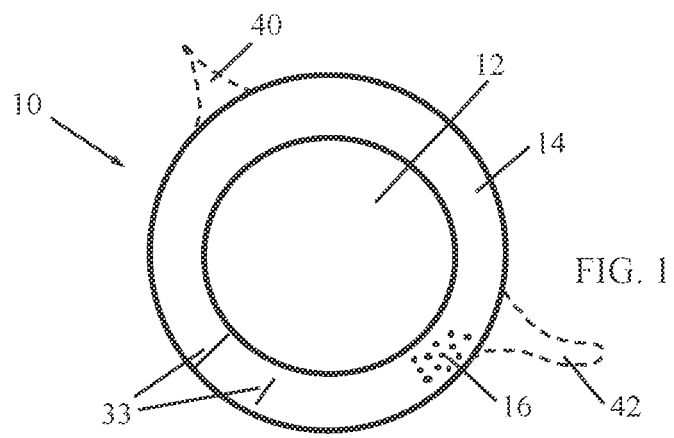
FIGS. 1 and 2 are simplified planar-view and edgewise-view illustrations, respectively, of a corneal implant, constructed and operative in accordance with a non-limiting embodiment of the present invention.
Figure 2:
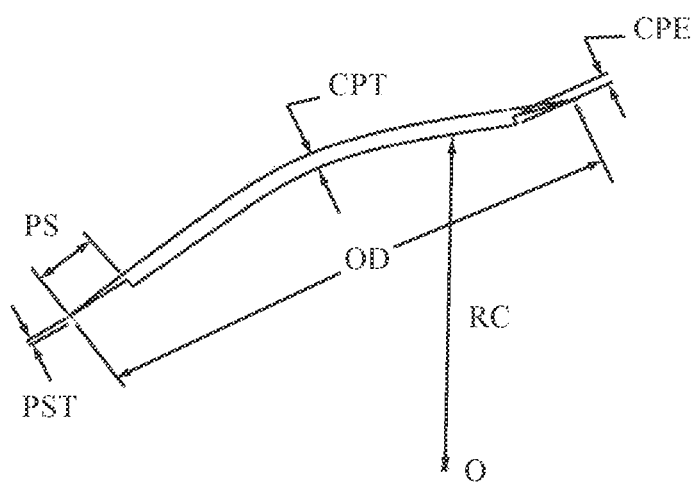

Reference is now made to FIGS. 1 and 2, which illustrate a corneal implant 10, constructed and operative in accordance with an embodiment of the present invention. The implant 10 may be a pseudo-endothelial implant, which can be used instead of an implant from a donor in a DSEK (Descemet Stripping Endothelial Keratoplasty) or DMEK (Descemet Membrane Endothelial Keratoplasty) surgery. Implant 10 serves as a water barrier enabling the dehydration of the cornea.

Implant 10 may be constructed of a clear, transparent, biologically compatible material, such as but not limited to, polymethylmethacrylate (PMMA), silicone, silicone rubber, collagen, hyaluronic acid (including the sodium, potassium and other salts thereof), hydrogel, such as acrylic or methacrylic hydrogels, e.g., hydroxyethyl methacrylate or methacrylic acid copolymer/partially hydrolyzed poly(2-hydroxyethyl methacrylate) (known as PolyHEMA), polysulfones, thermolabile materials and other relatively hard or relatively soft and flexible biologically inert optical materials, or any combination of such materials, such as a gel encapsulated in a polymer. Implant 10 may thus be rigid, semi-rigid or foldable, for example.

Some or all of implant 10 may be hydrophilic or hydrophobic.

In one aspect of the invention, corneal implant 10 has a central portion 12 of about 4 mm in diameter ("about" is ±10%) and a peripheral skirt 14 extending outwards from the central portion 12. The central portion 12 may be transparent and may or may not have optical properties, such as positive or negative magnification, astigmatism correction, refraction adjustment and others.

The peripheral skirt 14 may be made of the same material as central portion 12. Alternatively, peripheral skirt 14 may be made of a different material than central portion 12 and bonded or otherwise attached to central portion 12. The peripheral skirt 14 may be transparent but can instead be opaque.

In one aspect of the invention, at least a portion of the peripheral skirt 14 includes a mesh 16 that enables cell growth in and through the mesh to enhance adhesion of the implant to the cornea. The mesh 16 may have openings of equal or different sizes Non-limiting dimensions of the implant are as follows, using the nomenclature shown in FIG. 2:

Outer diameter of implant 10 (OD): 4.2-7.0 mm
Maximum thickness of central portion 12 (CPT): 25-75 µm
Peripheral width of peripheral skirt 14 (PS): 0.1-1.5 mm
Minimum thickness of peripheral skirt 14 (PST): 0-25 µm
Extra thickness of central portion 12 more than skirt 14 (CPE): 0-75 µm
Radius of curvature (RC) of implant from radius origin O: 6-10 mm Accordingly, peripheral skirt 14 may have a different thickness than the central portion 12 or may be the same thickness.

As another alternative, peripheral skirt 14 may be formed with one or more radial slits 33, which may extend the entire width of peripheral skirt 14 or just a portion of the width.

As another alternative, peripheral skirt 14 may include one or more radially extending portions 40 or 42 (shown in broken lines), which may be curved or straight with pointed on non-pointed ends.

The increased adhesion of peripheral skirt 14 may create a bond between the implant and the corneal tissue without the need for application of an external adhesive substance.

What is claimed is:
1. An apparatus comprising:
    a corneal implant comprising a central portion and a peripheral skirt extending radially outwards from said central portion, wherein said peripheral skirt comprises an annular mesh having a circular periphery; and two or more radially extending portions that extend radially outwards from said circular periphery, wherein said mesh is configured to enable cell growth in and through said mesh to enhance adhesiveness of the implant to a cornea, and wherein said mesh has openings of different sizes, wherein said central portion is transparent, wherein said central portion has optical properties selected from the group consisting of positive magnification, negative magnification, astigmatism correction, and refraction adjustment, wherein said peripheral skirt has no optical properties, wherein said peripheral skirt comprises one or more radial slits, and wherein said two or more radially extending portions includes at least one radially extending portion having a non-pointed end and at least one radially extending portion having a pointed end.

2. The apparatus according to claim 1, wherein said central portion is 4 mm±10% in diameter.

3. The apparatus according to claim 1, wherein said central portion has astigmatism correction.

4. The apparatus according to claim 1, wherein said central portion has refraction adjustment.

5. The apparatus according to claim 1, wherein said peripheral skirt and said central portion are made of identical materials.

6. The apparatus according to claim 1, wherein said peripheral skirt and said central portion are made of different materials.

7. The apparatus according to claim 1, wherein said peripheral skirt is opaque.

* * * * *